United States Patent [19]

VandenBerg

[11] Patent Number: Plant 6,945

[45] Date of Patent: Jul. 25, 1989

[54] CHRYSANTHEMUM PLANT NAMED YELLOW TAN

[75] Inventor: Cornelis P. VandenBerg, Salinas, Calif.

[73] Assignee: Yoder Brothers, Inc., Barberton, Ohio

[21] Appl. No.: 218,985

[22] Filed: Jul. 14, 1988

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Yellow Tan particularly characterized by its flat capitulum form; daisy capitulum type; yellow ray floret color; diameter across face of capitulum of up to 7.0 cm at maturity when grown as a pinched spray pot mum; uniform eight week photoperiodic flowering response to short days; medium plant height when grown as a pinched pot mum; and semi-spreading branching pattern.

3 Drawing Sheets

The present invention comprises a new and distinct cultivar of Chrysanthemum, botanically known as *Dendranthema grandiflora,* and referred to by the cultivar name Yellow Tan.

Yellow Tan, identified as 79P62C18, is a product of a mutation induction program which had the objective of creating new Chrysanthemum cultivars that would expand the color range of an existing cultivar while retaining all other traits.

Yellow Tan was discovered and selected by Cornelis P. VandenBerg on Oct. 24, 1985 in a controlled environment in Salinas, Calif. as one flowering plant within a flowering block established as rooted cuttings from stock plants which had been exposed as unrooted cuttings to an X-ray source of 2000 rads. The irradiated parent was the cultivar identified as Tan, disclosed in U.S. Plant Pat. No. 5,619.

The first act of asexual reproduction of Yellow Tan was accomplished when vegetative cuttings were taken from the initial selection in January 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Yellow Tan are firmly fixed and are retained through successive generations of asexual reproduction.

Yellow Tan has not been observed under all possible environmental conditions. The phenotype may vary significantly with variations in environment such as temperature, light intensity, and daylength.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Yellow Tan, which, in combination, distinguish this Chrysanthemum as a new and distinct cultivar:

1. Flat capitulum form.
2. Daisy capitulum type.
3. Yellow ray floret color.

4. Diameter across face of capitulum up to 7.0 cm at maturity, when grown as a pinched spray pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Semi-spreading branching pattern.

The accompanying photographic drawings show typical inflorescence and leaf characteristics of Yellow Tan, with the colors being as nearly true as possible with illustrations of this type.

Sheet 1 is a color photograph of Yellow Tan grown as a pinched spray pot mum.

Sheet 2 is a black and white photograph of three views of the inflorescence of Yellow Tan.

Sheet 3 is a black and white photograph showing the upper and under sides of the leaves of Yellow Tan at three stages of development (mature, intermediate and immature).

Of the commercial cultivars known to the inventor, the most similar in comparison to Yellow Tan is the parent cultivar Tan. All traits of Yellow Tan are similar to those of Tan, except the color of ray florets. Yellow Tan has a bright yellow ray floret color, while the color of Tan is greyed-orange.

In the following description, color references are made to The Royal Horticultural Society Colour Chart. The color values were determined on plant material grown as a pinched spray pot mum in Salinas, Calif. on Mar. 16, 1988.

Classification:

*Botanical.*—*Dendranthema grandiflora,* cv. Yellow Tan.

*Commercial.*—Daisy spray pot mum.

INFLORESCENCE

A. Capitulum:

*Form.*—Flat.

*Type.*—Daisy.

*Diameter across face.*—Up to 7.0 cm at maturity.

B. Corolla of ray florets:

*Color (general tonality from a distance of three meters).*—Yellow.

*Color (upper surface).*—9A.

*Color (under surface).*—6A.

*Shape.*—Flat, straight, oblong.

C. Corolla of disc florets:

*Color (mature).*—14A to 14B.

*Color (immature).*—144B to 144C.

D. Reproductive organs:

*Androecium.*—Present on disc florets only; moderate pollen.

*Gynoecium.*—Present on both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

*Branching pattern.*—Semi-spreading.

B. Foliage:

*Color (upper surface).*—137A to 137B.

*Color (under surface).*—137B to 137C.

*Shape.*—Lobed and slightly serrated.

I claim:

1. A new and distinct Chrysanthemum plant named Yellow Tan, as described and illustrated.

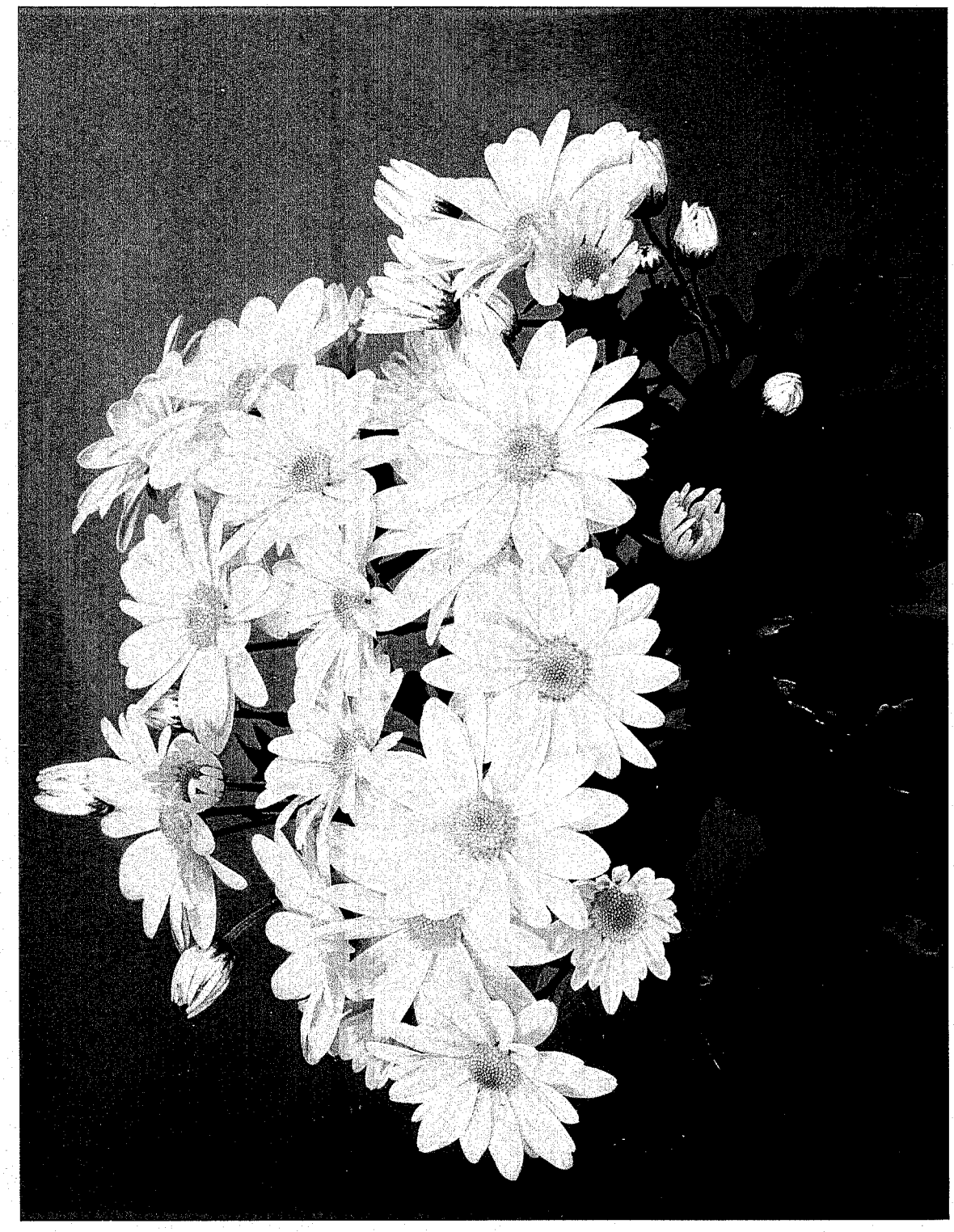

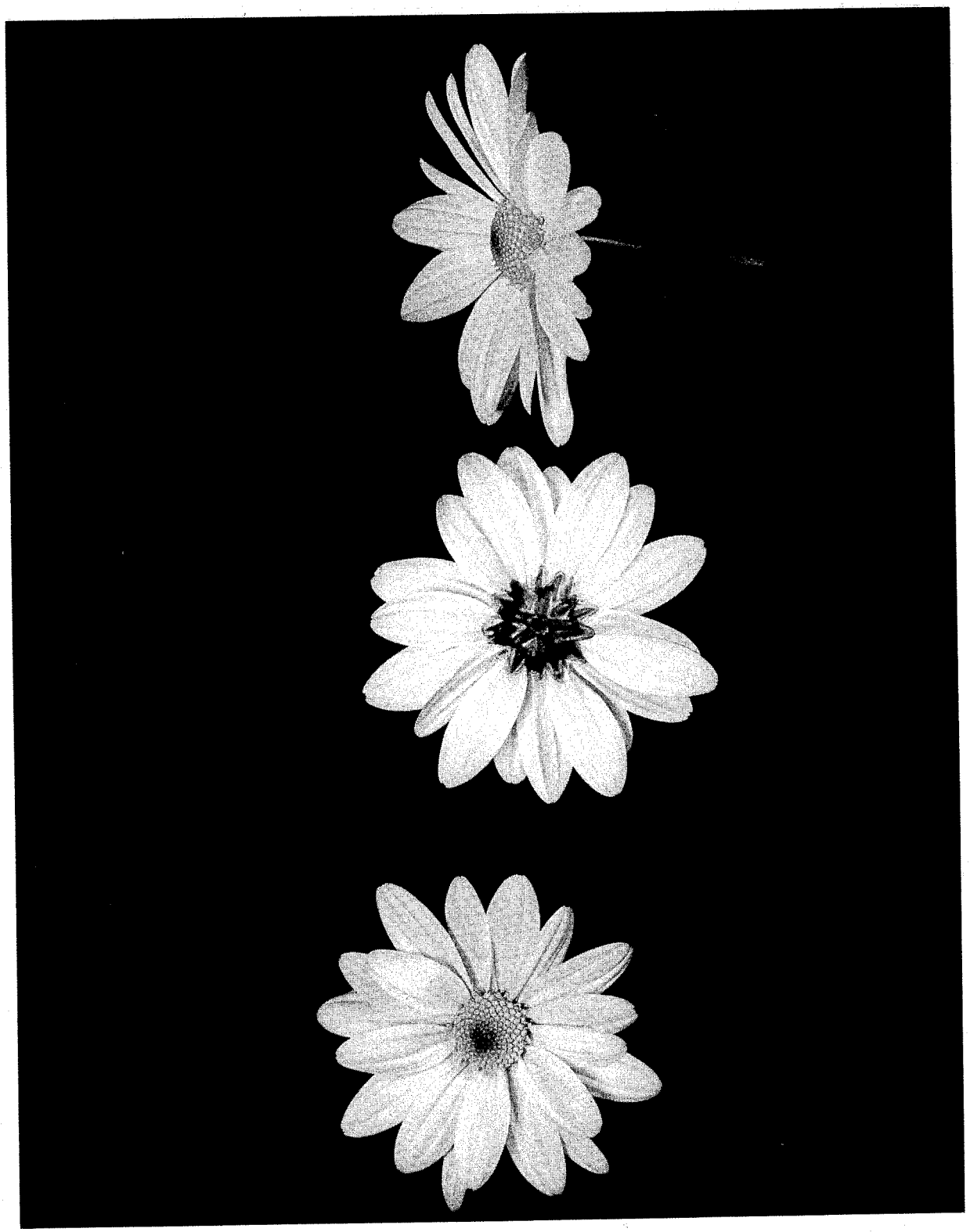

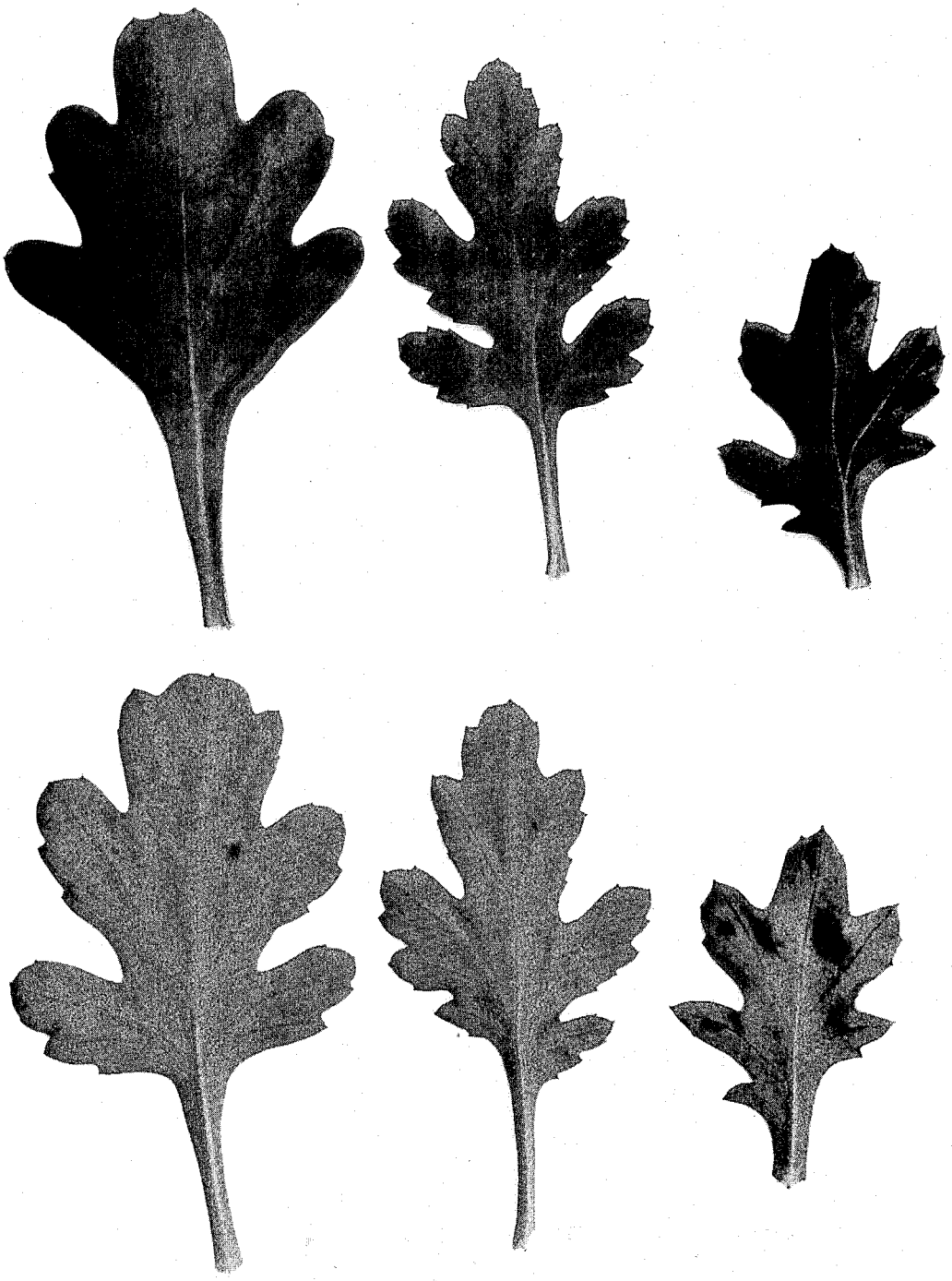

* * * * *